United States Patent
Harada et al.

(10) Patent No.: US 9,839,793 B2
(45) Date of Patent: Dec. 12, 2017

(54) PARTICLE THERAPY DEVICE AND METHOD FOR SETTING DOSE CALIBRATION FACTOR

(71) Applicant: Mitsubishi Electric Corporation, Chiyoda-ku, Tokyo (JP)

(72) Inventors: Hisashi Harada, Tokyo (JP); Masahiro Ikeda, Tokyo (JP); Osamu Takahashi, Tokyo (JP); Nobuhiko Ina, Tokyo (JP); Yuehu Pu, Tokyo (JP); Takaaki Iwata, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 297 days.

(21) Appl. No.: 14/771,444

(22) PCT Filed: Jun. 6, 2013

(86) PCT No.: PCT/JP2013/065686
§ 371 (c)(1),
(2) Date: Aug. 28, 2015

(87) PCT Pub. No.: WO2014/196052
PCT Pub. Date: Dec. 11, 2014

(65) Prior Publication Data
US 2016/0008631 A1   Jan. 14, 2016

(51) Int. Cl.
*A61N 5/10* (2006.01)

(52) U.S. Cl.
CPC ......... *A61N 5/1067* (2013.01); *A61N 5/1071* (2013.01); *A61N 5/1075* (2013.01);
(Continued)

(58) Field of Classification Search
CPC .. A61N 5/1067; A61N 5/1071; A61N 5/1075; A61N 5/1076; A61N 5/1087
(Continued)

(56) References Cited

U.S. PATENT DOCUMENTS

| 4,225,789 A * | 9/1980 | Albrecht ................ A61B 6/583 378/18 |
| 2011/0012028 A1* | 1/2011 | Harada ................ A61N 5/1075 250/492.1 |

(Continued)

FOREIGN PATENT DOCUMENTS

| JP | 10-314323 A | 12/1998 |
| JP | 2008-245716 A | 10/2008 |

(Continued)

OTHER PUBLICATIONS

International Search Report (PCT/ISA/210) dated Sep. 10, 2013, by the Japanese Patent Office as the International Searching Authority for International Application No. PCT/JP2013/065686.

*Primary Examiner* — Nicole Ippolito
(74) *Attorney, Agent, or Firm* — Buchanan Ingersoll & Rooney PC

(57) ABSTRACT

An irradiation apparatus radiates a particle beam after forming the beam for plural layers. A dose monitor measures a dose in real time. A dose evaluation unit evaluates an irradiation dose for each layer on the basis of a value measured by the dose monitor and a dose calibration factor set for each layer. An irradiation control section performs radiation control for each layer on the basis of an evaluation result of the dose evaluation unit. An interpolation value generation unit uses actual-measurement dose-calibration factors obtained by radiating a particle beam to a simulated phantom provided with a calibration dosimeter, to generate an interpolation estimation value of the dose calibration factor. For each layer subject to the interpolation value, and (Continued)

based on an irradiation condition of that layer, the interpolation value generation unit performs weighting on each of the actual-measurement dose-calibration factors.

20 Claims, 5 Drawing Sheets

(52) U.S. Cl.
CPC ............... *A61N 2005/1076* (2013.01); *A61N 2005/1087* (2013.01)

(58) Field of Classification Search
USPC ............ 250/396 R, 397, 492.1, 492.3; 600/1
See application file for complete search history.

(56) References Cited

U.S. PATENT DOCUMENTS

| | | |
|---|---|---|
| 2011/0049372 A1 | 3/2011 | Iseki et al. |
| 2012/0305756 A1* | 12/2012 | Russ .................. G06K 9/00543 250/252.1 |
| 2012/0313002 A1 | 12/2012 | Ikeda et al. |

FOREIGN PATENT DOCUMENTS

| | | |
|---|---|---|
| JP | 2010-032419 A | 2/2010 |
| JP | 2011-005276 A | 1/2011 |
| JP | 2011-050585 A | 3/2011 |
| JP | 2012-002772 A | 1/2012 |
| WO | WO 2009/139043 A1 | 11/2009 |
| WO | WO 2012/120636 A1 | 9/2012 |

* cited by examiner

PARTICLE THERAPY DEVICE AND METHOD FOR SETTING DOSE CALIBRATION FACTOR

TECHNICAL FIELD

The present invention relates to a particle therapy device for treating a cancer or the like, by radiating a particle beam thereto, and in particular, to a particle therapy device that employs a layer-stacking conformal irradiation method or a scanning irradiation method, as well as to a method for setting a dose calibration factor.

BACKGROUND ART

As an irradiation method employed in a particle therapy device, there is known: a layer-stacking conformal irradiation method in which an irradiation target is virtually partitioned into a plurality of layers in order of depth from the body surface and irradiation is performed for every layer; and a scanning irradiation method. In employing either irradiation method, it is required to precisely recognize a dose during irradiation in order to perform irradiation in line with a target dose planned by a treatment plan device; however, it is impossible to place (implant) a dosimeter in a body as the irradiation target. As a result, generally, the dose (actual dose) in the irradiation target is estimated based on a measurement value of a dose monitor placed upstream of the body surface in the traveling direction of the particle beam.

However, since the particle beam is not a parallel beam, but a fan beam or cone beam having a spread, variations in dose due to positional differences in the body within a diseased site are not reflected in the measurement value by the dose monitor, so that it is difficult to convert the value simply into an actual dose.

In this respect, there is disclosed a particle therapy device that performs calibration using a dose calibration factor that has been measured for every irradiation condition for treatment in consideration of influences not only by an atmospheric temperature and an atmospheric pressure but also a mechanical characteristic, on a relationship between the actual dose and the measurement value by the dose monitor (for example, see, Patent Document 1). Furthermore, there is also disclosed a particle therapy device that calculates a dose calibration factor for every layer in a layer-stacking conformal irradiation method or a scanning irradiation method (for example, see, Patent Document 2).

CITATION LIST

Patent Document

Patent Document 1: Japanese Patent Application Laid-open No. 2008-245716 (Paragraphs 0009 to 0025, FIG. 1 to FIG. 4)

Patent Document 2: Japanese Patent Application Laid-open No. 2011-5276 (Paragraphs 0025 to 0039, FIG. 7 to FIG. 9)

SUMMARY OF THE INVENTION

Problems to be Solved by the Invention

In the case of calculating a dose calibration factor, assuming as if a water phantom is an irradiation target, it is general to use a measurement value of a dosimeter (reference dosimeter) put into the water phantom and a measurement value of a dose monitor at the time of varying energy of the beam to be radiated or a depth of the reference dosimeter. However, since the water phantom itself has a restriction in size, there is a limitation in calculating the dose calibration factor corresponding to every layer using the water phantom. Specifically, there is a problem that it is unable to make actual measurement when the depth (water-equivalent depth) for measurement is deeper than an allowable depth for measurement by the water phantom.

Moreover, even when every layer set in the irradiation target to be irradiated is in a range of the water-equivalent depth that is allowable for measurement by the water phantom, the pitch in water-equivalent depth of each layer is small to fall in an order from little less than 1 mm to several mm. Thus, assuming that the thickness of the irradiation target is, for example, 75 mm, it is necessary to perform actual measurements for as many as from about 30 to 100 times, and thus, there is also a problem of taking a lot of trouble and time.

The present invention has been made to solve the problems as described above, and an object thereof is to provide a particle therapy device and a calibration method of an irradiation dose by which a highly accurate irradiation in line with a treatment plan is achieved.

Means for Solving the Problems

The particle therapy device of the invention is a particle therapy device in which an irradiation target is partitioned into a plurality of layers in order of depth from a body surface, and irradiation is performed while an irradiation dose is controlled for each of the layers, which is characterized by comprising: an irradiation apparatus that radiates a particle beam supplied from an accelerator, after forming the beam for said each of the layers; a dose monitor that is placed in the irradiation apparatus and measures a dose in real time; a dose evaluation unit that evaluates the irradiation dose for said each of the layers on the basis of a dose that is calculated using a measurement value measured by the dose monitor and using a dose calibration factor set for said each of the layers, and a dose determined by a treatment plan; an irradiation control device that controls a irradiation amount to said each of the layers on the basis of an evaluation result of the dose evaluation unit; and an interpolation value generation unit that uses actual-measurement dose-calibration factors each obtained by radiating a particle beam to a simulated phantom provided with a calibration dosimeter, to thereby generate an interpolation value or an estimation value of the dose calibration factor for at least one of the layers for which the actual-measurement dose-calibration factor is not obtained; wherein, for each layer subject to the interpolation value or the calibration value, based on an irradiation condition of that layer, the interpolation value generation unit performs weighting on each of the actual-measurement dose-calibration factors.

Further, the method for setting a dose calibration factor of the invention is a method for setting a dose calibration factor that is used in a particle beam therapy in which an irradiation target is partitioned into a plurality of layers in order of depth from a body surface and irradiation is performed while an irradiation dose is controlled for each of the layers, and that is for calculating a dose in the irradiation target using a measurement value of a dose monitor placed in an irradiation apparatus; which is characterized by comprising: a step of radiating a particle beam to a simulated phantom provided with a calibration dosimeter to thereby obtain actual-measurement dose-calibration factors each using a depth of the calibration dosimeter in the simulated phantom as a parameter, on the basis of the measurement value of the dose monitor and a measurement value of the calibration dosimeter; and an interpolation value generation step of establishing a mathematical function of the dose calibration factor having the depth as a variable, on the basis of the actual-measurement dose-calibration factors, to thereby generate an interpolation value or an estimation value of the dose calibration factor corresponding to a layer for which the actual-measurement dose-calibration factor is not obtained; wherein, in the interpolation value generation step, for the layer subject to the interpolation value or the calibration value, based on an irradiation condition corresponding to that layer, weighting is performed on each of the actual-measurement dose-calibration factors.

Effect of the Invention

According to the particle therapy device and the method for setting a dose calibration factor of the invention, since it is possible to precisely calibrate a dose even for a layer for which no actual dose has been measured, a highly accurate irradiation in line with the treatment plan can be achieved.

MODES FOR CARRYING OUT THE INVENTION

Embodiment 1

Figure 1:
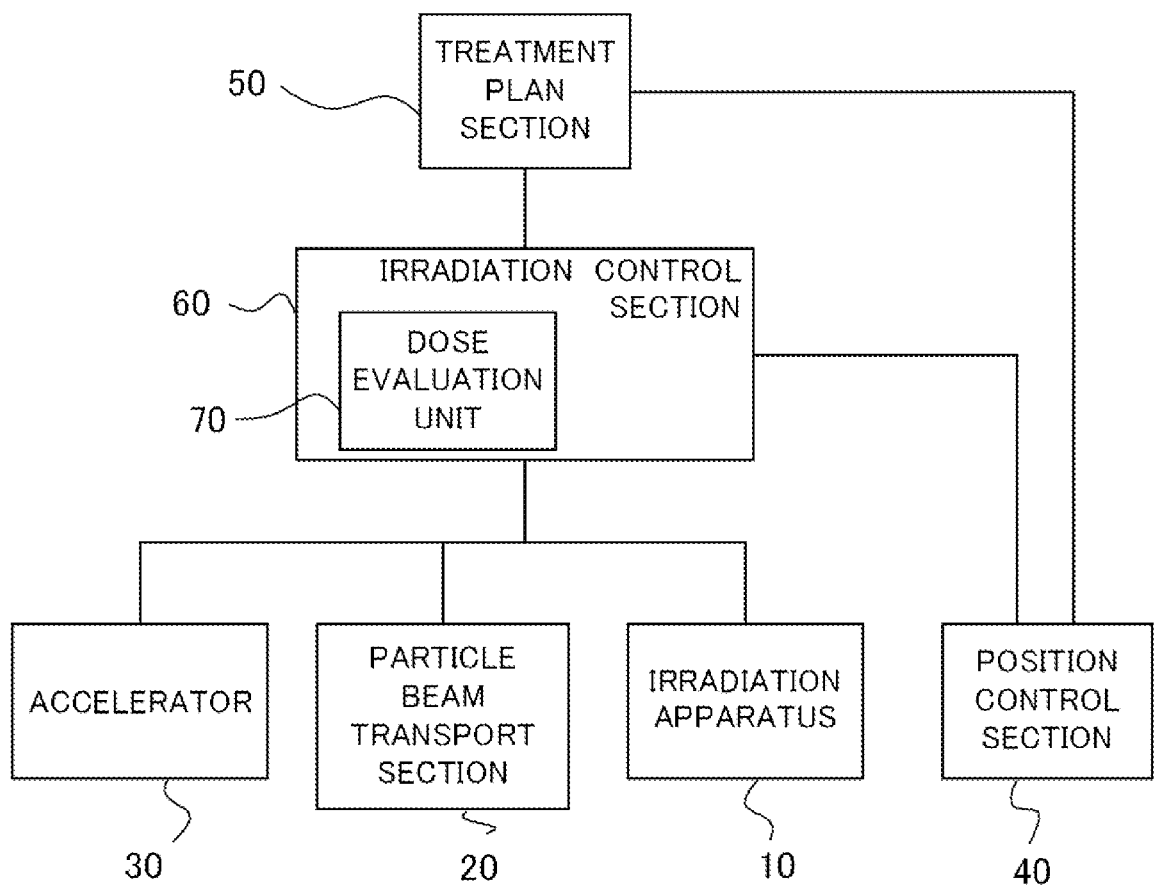
FIG. 1 is a block diagram for illustrating a configuration of a particle therapy device and a method for setting a dose calibration factor, according to Embodiment 1 of the invention.
Figure 2:
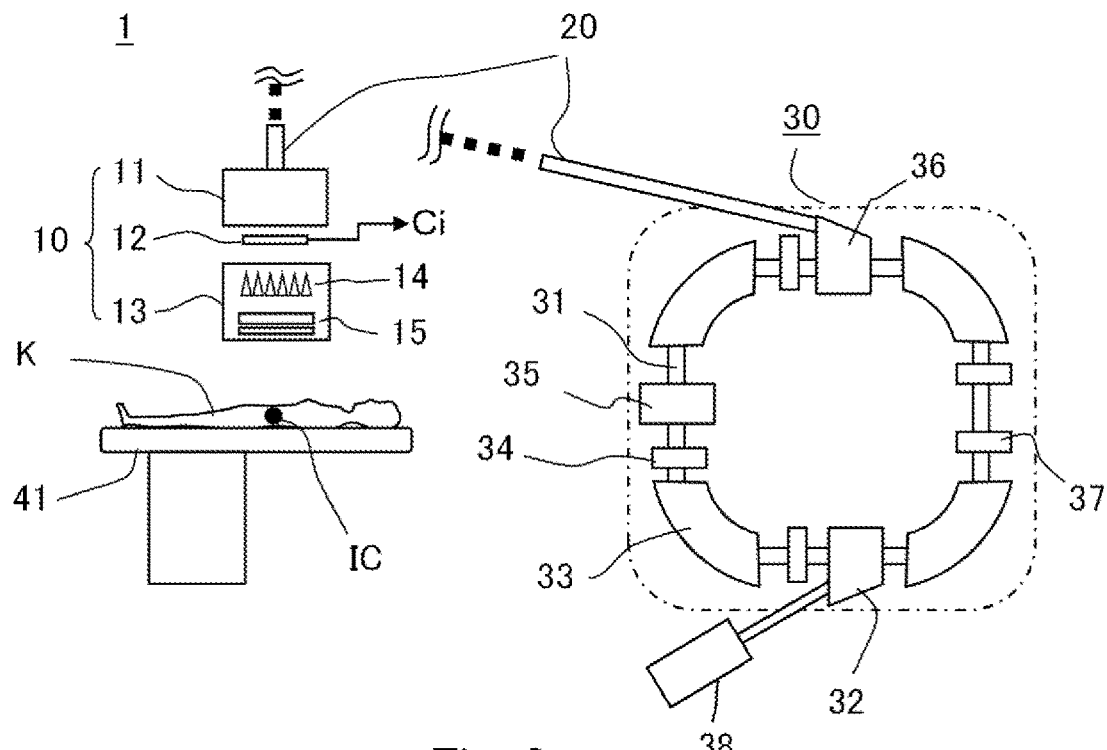
FIG. 2 is a diagram schematically showing apparatuses/instruments constituting the particle therapy device according to Embodiment 1 of the invention.
Figure 3:
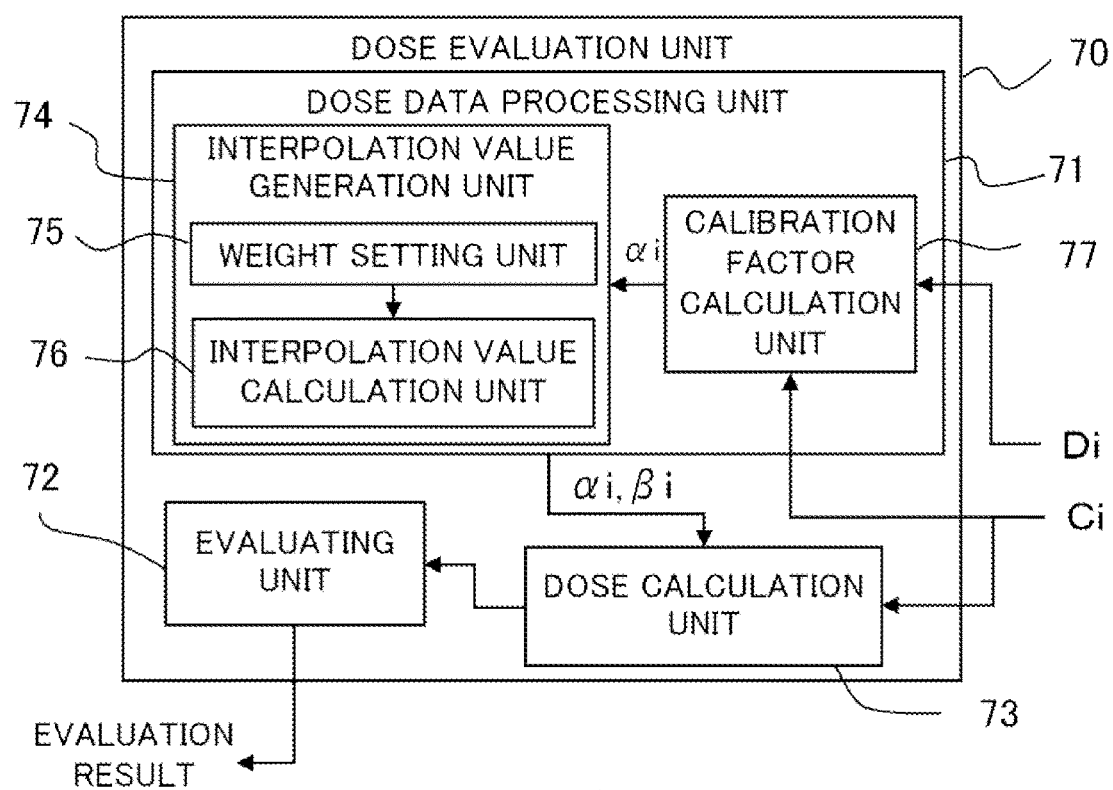
FIG. 3 is a block diagram for illustrating a configuration of a dose evaluation unit of the particle therapy device and the method for setting a dose calibration factor, according to Embodiment 1 of the invention.
Figure 4:
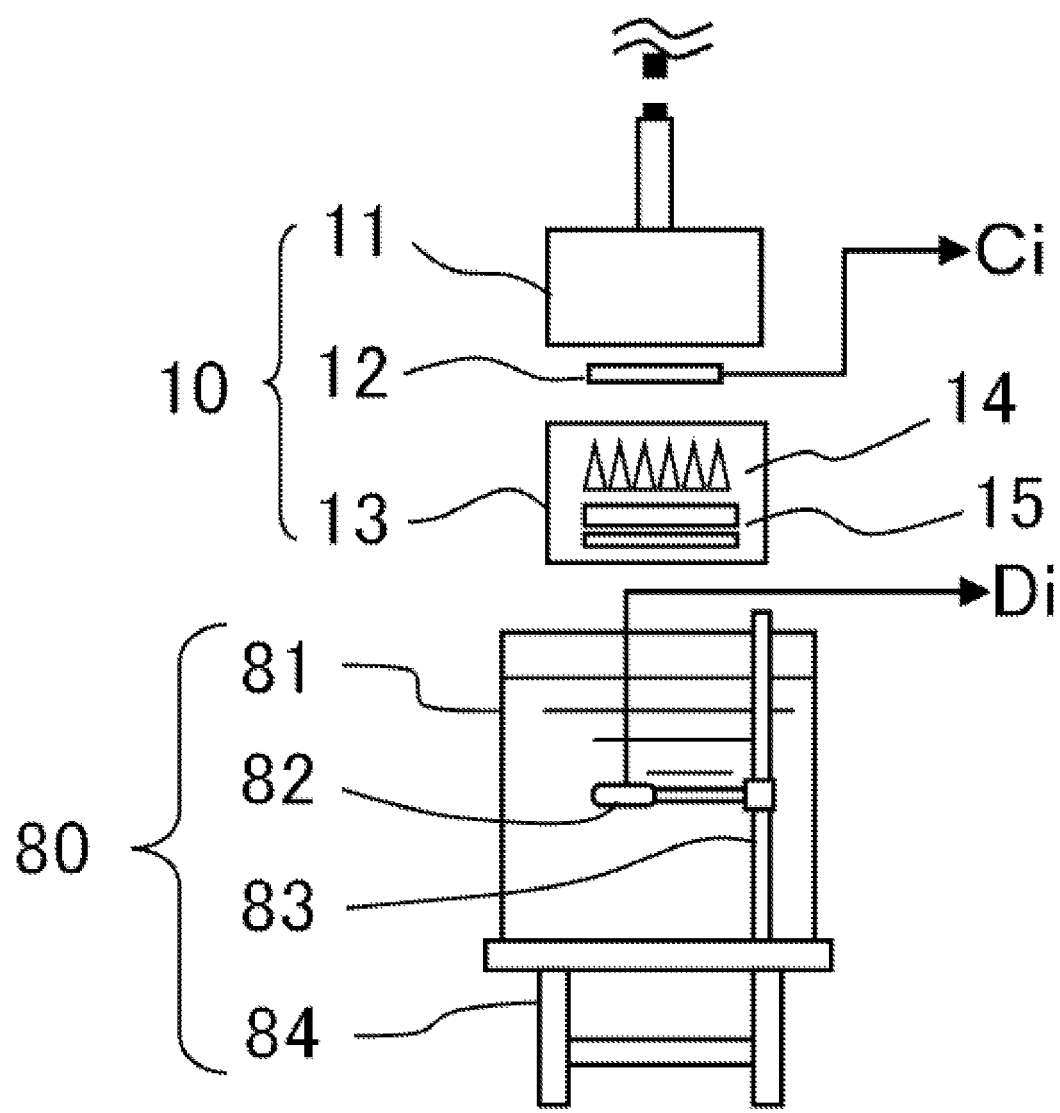
FIG. 4 is a diagram schematically showing an apparatus configuration at the time of performing a dose calibration in the particle therapy device according to Embodiment 1 of the invention.
Figure 5:
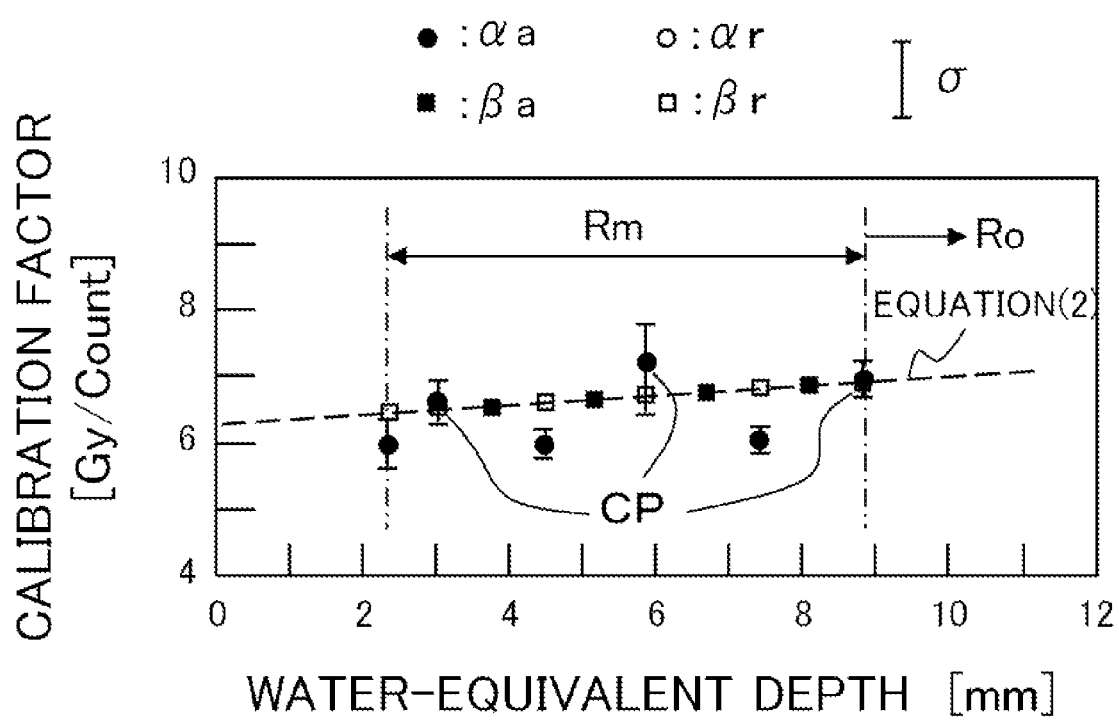
FIG. 5 is a graph representing a relationship among water-equivalent depths of respective layers, actually-measured dose calibration factors and interpolated dose calibration factors, with respect to the particle therapy device according to Embodiment 1 of the invention.

Hereinafter, description will be made about a configuration of a particle therapy device according to Embodiment 1 of the invention. FIG. 1 to FIG. 5 are for illustrating the particle therapy device and a method for setting a dose calibration factor, according to Embodiment of the invention, in which FIG. 1 is an overall functional-block diagram for illustrating a configuration of the particle therapy device and the method for setting a dose calibration factor; FIG. 2 is an overall diagram for schematically illustrating an apparatus configuration at the time of performing a particle beam therapy; FIG. 3 is a functional block diagram of a dose evaluation unit, for illustrating a configuration of the particle therapy device and the method for setting a dose calibration factor; FIG. 4 is a diagram for illustrating an apparatus configuration at the time of performing a dose calibration in a calibration stage; and FIG. 5 is a graph for calculating a dose calibration factor for making an irradiation dose, in which represented is a relationship among water-equivalent depths of respective layers, actually-measured dose calibration factors and interpolated dose calibration factors.

The particle therapy device and the method for setting a dose calibration factor according to Embodiment 1 of the invention are characterized by a configuration for generating an interpolation value or an estimation value for precisely evaluating an irradiation dose in a layer for which no actual dose has been measured. However, prior to the description of that configuration, description will be made about a configuration of the particle therapy device for virtually partitioning an irradiation target into a plurality of layers in order of depth from a body surface to thereby perform irradiation for every layer, and an apparatus configuration at the time of obtaining a dose calibration factor. Note that, hereinafter, for simplifying the description, the interpolation value and the estimation value are referred collectively to as an interpolation value.

As shown in FIG. 2, a particle therapy device 1 according to Embodiment 1 of the invention includes: as a supply source of a particle beam (beam source), an accelerator 30 which is a synchrotron; an irradiation apparatus 10 that radiates the particle beam supplied from the accelerator 30 after forming the beam according to a diseased site (irradiation target); and a particle beam transport section 20 that connects the accelerator 30 with a plurality of irradiation apparatuses 10 (including one not shown in the figure) and transports the particle beam emitted from the accelerator 30 to the selected irradiation apparatus 10.

The accelerator 30 includes a vacuum duct 31 that provides a trajectory channel for causing charged particles to go around therethrough; an injection device 32 for injecting the charged particles supplied from a pre-accelerator 38 into the vacuum duct 31; bending magnets 33 for deflecting the trajectory of the charged particles so that the charged particles circulate along the round trajectory in the vacuum duct 31; a convergence electromagnet 34 that causes the charged particles on the round trajectory to converge so as not to diverge; a high-frequency acceleration cavity 35 that applies to the circulating charged particles, a high frequency voltage synchronous with the particles to thereby accelerate them; an emission device 36 for taking out from the round trajectory the charged particles accelerated in the round trajectory, as a particle beam having a predetermined energy, so as to emit it to the particle beam transport section 20; and a six-pole electromagnet 37 that excites resonance in the round trajectory for emitting the particle beam from the emission device 36. Here, the charged particles in the round trajectory are accelerated by a high frequency electric field up to approx. 60% to 80% of the light velocity while being bent by the magnets, and emitted to the particle beam transport section 20.

The particle beam transport section 20 is referred to as HEBT (High Energy Beam Transport) system, and includes a vacuum duct that provides a transport channel of the particle beam; a switching electromagnet for switching the trajectory of the particle beam; and a bending magnet for deflecting the particle beam by a predetermined angle. Note that, in the figure, illustration is omitted about portions in the particle beam transport section 20 other than vacuum-duct portions connected to a connection part to the accelerator 30 and connected to the irradiation apparatus 10.

The irradiation apparatus 10 is placed in each of unshown treatment chambers for applying a particle beam therapy to a patient K, and serves to radiate the particle beam supplied from the particle beam transport section 20 to the diseased site after forming the beam into an irradiation field matched to the size and depth of the irradiation target. However, the particle beam supplied to the irradiation apparatus 10 is a so-called pencil-like narrow beam. For this reason, the irradiation apparatus 10 is provided with a lateral-direction irradiation-field forming unit 11 for controlling, in the irradiation field of the particle beam, a shape in a lateral direction (namely, in a plane perpendicular to a beam traveling direction), a depth-direction irradiation-field forming unit 13 for controlling in that field a shape in a depth direction (namely, in the beam traveling direction), and a dose monitor 12 for monitoring (counting) the particle beam passing a given region in real time to thereby output a measurement value $C_i$ in order to evaluate a dose radiated to the diseased site. Further, in the treatment chamber, a treatment table 41, etc. for positioning and fastening the patient K under radiation, are provided with reference to an isocenter IC.

In the depth-direction irradiation-field forming unit 13, there are included, for example, a ridge filter 14 for spreading the width of the Bragg peak, a range shifter 15 for changing the energy (range) of the particle beam, and the like. In the lateral-direction irradiation-field forming unit 11, there are included, for example, an unshown scanning electromagnet for deflecting the particle beam in a direction perpendicular to the beam traveling direction, and the like. There are cases where the irradiation field is subjected to forming directly by the scanning electromagnet and where it is once enlarged, for example, into a circular shape by the scanning electromagnet and then subjected to forming using a limiter such as a multileaf collimator or the like.

When the therapy is performed using such a particle therapy device 1, it is necessary to control its respective parts in their cooperative manner. Thus, in terms of control, the particle therapy device 1 is represented as being configured with a treatment plan section 50, an irradiation control section 60, the accelerator 30, the particle beam transport section 20, the irradiation apparatus 10, a position control section 40, and the like, as shown in FIG. 1.

The irradiation apparatus 10 has, as described above, a function for forming a proper irradiation field at the time of radiating the particle beam to the patient, and the treatment plan section 50 has a function of determining parameters of the respective devices in the irradiation apparatus 10 as proper values, in order to radiate with an intended dose distribution. The position control section 40 has functions of executing fastening of the patient using the treatment table 41, etc., positioning and confirmation of a target (referred to also as a target volume) and the like. The irradiation control section 60 controls operations of the accelerator 30, the particle beam transport section 20, the irradiation apparatus 10 and the position control section 40, on the basis of the instructions from the treatment plan section 50. Note that, prior to the description of a detailed configuration (FIG. 3) of the irradiation control section 60, a flow of the particle beam therapy will be described.

Here, the particle beam therapy is described separately as three stages. The three stages are (i) treatment planning stage, (ii) calibration stage, and (iii) irradiation treatment stage.

In the treatment planning stage (i), by the treatment plan section 50 (or an external treatment plan device), a plan is made regarding 1: from what angle, 2: with what irradiation field, and 3: with what dose, the radiation is to be applied to the diseased site of the patient that is the irradiation target.

In the calibration stage (ii), as shown in FIG. 3, a dose calibration factor for converting a measurement value detected by the dose monitor 12 into a dose given to the irradiation target, is calculated by a dose evaluation unit 70 established in the irradiation control section 60. Specifically, as shown in FIG. 4, as a simulated phantom that simulates a human body, a calibration device 80 including a water phantom 81 is placed at the position where the treatment table 41 is to be placed at the time of treatment. In the water phantom 81 placed on a height adjusting table 84, a calibration dosimeter 82 is placed that is to be positioned by a dosimeter actuating device 83, at a position corresponding to each of the layers that are set in order of depth from the body surface of the irradiation target. Then, a beam for calibration (correction) is radiated to the water phantom 81. At that time, the measurement value $C_i$ to be outputted from the dose monitor 12 permanently installed in the irradiation apparatus 10 and a physical dose $D_i$ to be outputted from the calibration dosimeter 82 are actually measured, so that a dose calibration factor $\alpha_i$ represented by the formula (1) is calculated for each layer (each depth of the calibration dosimeter 82 from the water surface) by a calibration factor calculation unit 77.

[Equation 1]

$$\alpha_i(x_i) := \frac{D_i}{C_i}, \quad i = 1, 2, 3, \ldots n \tag{1}$$

Here, a subscript i is an index indicative of an i-th layer, and the dose calibration factor $\alpha_i$ [Gy/Count] is calculated as a value resulted from dividing the physical dose $D_i$ [Gy] actually measured with the beam for calibration using the calibration dosimeter 82, by the measurement value $C_i$ [Count] measured by the dose monitor 12 at that time. The calculated dose calibration factor $\alpha_i$ for each layer is stored, as in a look-up table using the water-equivalent depth xi [mm WEL] for each layer as a parameter, in a dose data processing unit 71.

In the particle therapy device or the method for setting a dose calibration factor according to Embodiment 1, there resides a feature in a configuration for precisely calculating an interpolation value $\beta_i$ [Gy/Count] that is an estimation value of the dose calibration factor with respect to a layer corresponding to a region at the depth for measurement that is deeper than the allowable depth for measurement by the water phantom 81. What is meant specifically is to vary the weight of each of the dose calibration factor $\alpha_i$ depending the water-equivalent depth $x_i$ at the time of establishing a function (mathematical model) for the interpolation value $\beta_i$ corresponding to a given water-equivalent depth $x_j$, using the dose calibration factor $\alpha_i$ based on the actually measured data.

For simplifying description, firstly, an example will be shown about a case where, regardless of weighting, the function (mathematical model) is established by the polynomial equation represented by the formula (2), followed by calculating unknown coefficients of the polynomial equation using a least-square method.

$$\beta_i = k_0 + k_1 x_i + k_2 x_i^2 \tag{2}$$

It should be noted that $k_0$, $k_1$, $k_2$ are unknown coefficients, which are, when A and B are defined as in the following formula (D1), calculated as represented by the formula (3).

[Equation 2]

$$A := \begin{bmatrix} 1 & x_1 & x_1^2 \\ 1 & x_2 & x_2^2 \\ \vdots & \vdots & \vdots \\ 1 & x_n & x_n^2 \end{bmatrix} \quad B := \begin{bmatrix} \alpha_1 \\ \alpha_2 \\ \vdots \\ \alpha_n \end{bmatrix} \quad (D1)$$

$$[k_0 \quad k_1 \quad k_2] = : X = (A^T A)^{-1} A^T B \quad (3)$$

Further note that the superscript T represents a transposed matrix.

Although the degree of the polynomial equation may be increased or decreased as appropriate, the inventors have confirmed experimentally that, when there is a consecutive relationship between a depth of the layer and an irradiation dose, the dose calibration factor can be estimated sufficiently accurately if the polynomial equation of second order is used. However, focusing on the fact that there are many cases in the particle beam therapy where a non-consecutive relationship arises between a depth of the layer and an irradiation dose, the inventors cause the weight of each dose calibration factor $\alpha_i$ to vary depending on the water-equivalent depth $x_i$, at the generation of the interpolation value $\beta_i$.

Thus, in the dose data processing unit 71, as shown in FIG. 3, there is provided in an interpolation value generation unit 74, a weight setting unit 75 for setting a weight of each dose calibration factor $\alpha_i$ on the basis of the water-equivalent depth $x_i$ for the interpolation value $\beta_i$. This causes an interpolation value calculation unit 76 to calculate using the dose calibration factor $\alpha_i$, the interpolation value $\beta_i$ by the function in which the weights set by the weight setting unit 75 are reflected. More specifically, in consideration of the fact that, in many cases, a region corresponding to a distal-side layer mostly becomes deeper than a measurement depth allowable for measurement by the water-phantom 81, thus making the actual measurement unable, each unknown coefficient of the function is calculated using a weighted least-square method in which distal-side data is heavily weighted.

Namely, instead of the aforementioned combination of the formula (D1) and the formula (3), unknown coefficients $k_0$, $k_1$, $k_2$ are calculated by the combination of the formula (D2) and the formula (4).

[Equation 3]

$$A := \begin{bmatrix} 1 & x_1 & x_1^2 \\ 1 & x_2 & x_2^2 \\ \vdots & \vdots & \vdots \\ 1 & x_n & x_n^2 \end{bmatrix} \quad B := \begin{bmatrix} \alpha_1 \\ \alpha_2 \\ \vdots \\ \alpha_n \end{bmatrix} \quad W := \begin{bmatrix} 1 & & & & 0 \\ & \ddots & & & \\ & & 1 & & \\ & & & 2 & \\ & & & & 5 \\ 0 & & & & 10 \end{bmatrix} \quad (D2)$$

$$[k_0 \quad k_1 \quad k_2] = : X = (A^T W^T W A)^{-1} A^T W^T W B \quad (4)$$

In the formula (D2), W represents a diagonal matrix in which the numerals arranged from upper left to lower right represent weights, thus revealing that the weights (=2, 5, 10) set for lower-right deep layers (in the distal side) are made larger than the weight (=1) set for upper-left shallow layers (in the proximal side).

Each function (mathematical model) for estimating the dose calibration factor, including such a definition of W, is generated depending on the water-equivalent depth $x_i$ for calculating the interpolation value $\beta_i$ and is being stored in the interpolation value generation unit 74. Then, in the weight setting unit 75, at the time of calculating the interpolation value $\beta_i$ for a layer deeper than the measurement allowable range, the function in which the weight is made larger at a distal side is used, whereas in the case within the measurement allowable range, the function in which weighting is made in a flattened manner or the function in which the weight is made large for a layer near to the depth of that range, is used. Namely, the weight setting unit 75 is configured so that it can appropriately select or modify the function depending on the water-equivalent depth $x_i$ for calculating $\beta_i$.

In the irradiation treatment stage (iii), during radiation to the irradiation target, the measurement value $C_i$ outputted in real time by the dose monitor 12 is outputted to a dose calculation unit 73 in the dose evaluation unit 70. The dose calculation unit calculates from the measurement value $C_i$, the irradiation dose given to the irradiation target ($C_i \times \alpha_i$, or $C_i \times \beta_i$) using the dose calibration factor $\alpha_i$ or the interpolation value $\beta_i$ generated in the calibration stage and corresponding to that layer, and outputs it to an evaluating unit 72. At the evaluating unit 72, it is determined whether or not the outputted dose has reached a target dose, and such an evaluation result is outputted. This makes it possible to perform evaluation of dose in real time, thus allowing an irradiation control to be performed based on the evaluation result.

In order to accomplish irradiation consistent with the target dose, the irradiation control section 60, upon receiving the evaluation result indicating that the dose in that layer has reached the target dose, controls operation of the irradiation apparatus 10 to stop irradiation at that layer followed by shifting toward the next layer.

It should be noted that, calculating the aforementioned interpolation value $\beta_i$ corresponding to the water-equivalent depth $x_i$ makes it possible to precisely calculate the dose of the layer whose dose calibration factor $\alpha_i$ is difficult to obtain based on an actual measurement value. Meanwhile, as represented by the polynomial equation of the formula (2), the interpolation value $\beta_i$ is a value that varies consecutively with respect to the depth direction, so that it is advantageous, in terms of performing control, to use only the interpolation value $\beta_i$ even for the region with presence of the dose calibration factor $\alpha_i$. However, in actual irradiation, as shown in FIG. 5, there is a case of exhibiting a property deviated from the polynomial equation represented by the formula (2). Thus, in accordance with the particle therapy device or the irradiation-dose calibration method according to Embodiment 1, it is configured/designed so as to be able to select as to which one of the data of the dose calibration factor $\alpha_i$ and that of the interpolation value $\beta_i$ is to be used, for the region with presence of the dose calibration factor $\alpha_i$.

A specific example thereof will be described using FIG. 5. In the figure, the abscissa represents the water-equivalent depth $x_i$ [mm WEL] (the depth of the calibration dosimeter 82 in the water phantom 81 from the water surface) and the ordinate represents the dose calibration factor $\alpha_i$ or the interpolation value $\beta_i$ [Gy/Count]. Note that, in the figure, $\alpha a$ is dose calibration factor $\alpha_i$-data selected for dose calibration, $\alpha r$ is dose calibration factor $\alpha_i$-data not selected for dose calibration, and a broken line is a curve representing the formula (2) and determined using the unknown coefficients that have been calculated while performing weighting on the dose calibration factor $\alpha_i$. Further, βa is interpolation value $\beta_i$-data selected for dose calibration and is interpolation value $\beta_i$-data not selected for dose calibration.

In the figure, such a case is shown where, for the layer with presence of the dose calibration factor $\alpha_i$, the interpolation value $\beta_i$ is not selected but the dose calibration factor $\alpha_i$ is selected. However, if the interpolation value $\beta_i$ corresponds as a value to the data within a range of a variation σ of the dose calibration factor $\alpha_i$ (CP, in the figure), the interpolation value $\beta_i$ may be selected in place of the dose calibration factor $\alpha_i$.

Instead, the above selection may be done based on a signal from an input screen in the irradiation control section 60. Specifically, a doctor/technician who operates the particle therapy device 1, an operator who operates the system based on an instruction by a doctor, etc. or the like, confirms which layer(s) (which order number layer(s)), the diseased site of the patient, as an irradiation target, corresponds to. For example, in the case where, as such corresponding layer(s), those with the indexes i=10 to 30 are corresponding thereto, when the determination whether to use the dose calibration factor $\alpha_i$ stored in the lookup table or to use the interpolation value $\beta_i$ based on the function, is done for each of the layers on the input screen in the irradiation control section 60, its result is outputted to the dose data processing unit 71.

In either instance, when a calibration depth about the patient with respect to a shot at a distal side is placed in a region Ro that is deeper than the depth region Rm allowable for measurement by the water phantom and thus not allowed at all for actual measurement, namely, when there is no corresponding dose calibration factor $\alpha_i$ in the lookup table, this results in using the interpolation value $\beta_i$, automatically.

Consequently, it becomes possible to perform dose evaluation ensuring both smoothness in control and preciseness. Note that, in the above example, description has been made about a case where the dose evaluation unit 70 is established in the irradiation control section 60 and the calibration factor calculation unit 77, etc. are established in the dose evaluation unit 70; however, its modification is of course be possible as appropriate, so long as capable of exhibiting the performance described above.

As described above, in accordance with the particle therapy device according to Embodiment 1, there is provided a particle therapy device 1 in which an irradiation target is partitioned into a plurality of layers in order of depth from a body surface, and irradiation is performed while an irradiation dose is controlled for each of the layers, said particle therapy device configured to include: the irradiation apparatus 10 that radiates a particle beam supplied from the accelerator 30, after forming the beam for said each of the layers; the dose monitor 12 that is placed in the irradiation apparatus 10 and measures a dose in real time; the dose evaluation unit 70 that evaluates the irradiation dose for said each of the layers on the basis of a dose that is calculated using the measurement value $C_i$ measured by the dose monitor 12 and using the dose calibration factor ($\alpha_i$, $\beta_i$) set for said each of the layers, and a dose determined by a treatment plan; an irradiation control device (the irradiation control section 60) that controls a irradiation amount to said each of the layers on the basis of an evaluation result of the dose evaluation unit 70; and the interpolation value generation unit 74 that uses actual-measurement dose-calibration factors $\alpha_i$ each obtained by radiating a particle beam to a simulated phantom (the water phantom 81) provided with the calibration dosimeter 82, to thereby generate the interpolation value $\beta_i$ of the dose calibration factor for at least one of the layers for which the actual-measurement dose-calibration factor $\alpha_i$ is not obtained;

wherein, at the time of generating the interpolation value $\beta_i$ for the layer whose depth $x_i$ is deeper than a predetermined value (for example, a measuring limit by the water phantom 81), the interpolation value generation unit 74 performs weighting so that a weight of the actual-measurement dose-calibration factor $\alpha_i$ at a deep layer among the actual-measurement dose-calibration factors $\alpha_i$ is larger than a weight of the actual-measurement dose-calibration factor $\alpha_i$ at a shallow layer there among. Thus, even for the layer whose depth $x_i$ is deeper than the predetermined value and which is thus not allowed for measurement by the simulated phantom (water phantom 81), a precise interpolation value $\beta_i$ can be obtained and thus the dose can be calibrated precisely, so that it is possible to achieve a highly accurate irradiation in line with the treatment plan.

Further, in accordance with the method for setting a dose calibration factor according to Embodiment 1, there is provided a method for setting a dose calibration factor ($\alpha_i$, $\beta_i$), that is used in a particle beam therapy in which an irradiation target is partitioned into a plurality of layers in order of depth from a body surface and irradiation is performed while an irradiation dose is controlled for each of the layers, and that is for calculating a dose in the irradiation target using a measurement value $C_i$ of the dose monitor 12 placed in the irradiation apparatus 10;

said method is designed to include: a step of radiating a particle beam to a simulated phantom (water phantom 81) provided with the calibration dosimeter 82 to thereby obtain actual-measurement dose-calibration factors $\alpha_i$ each using a depth $x_i$ of the calibration dosimeter 82 in the simulated phantom (water phantom 81) as a parameter, on the basis of the measurement value $C_i$ of the dose monitor 12 and the measurement value (physical dose Di) of the calibration dosimeter 82; and an interpolation value generation step of establishing a mathematical function (formula (2)) of the dose calibration factor $\alpha_i$ having a depth $x_i$ as a variable, on the basis of the actual-measurement dose-calibration factors $\alpha_i$, to thereby generate the interpolation value $\beta_i$ of the dose calibration factor corresponding to the layer for which the actual-measurement dose-calibration factor $\alpha_i$ is not obtained;

wherein, in the interpolation value generation step, at the time of generating the interpolation value $\beta_i$ for the layer whose depth $x_i$ is deeper than a predetermined value (for example, a measuring limit by the water phantom 81), weighting is performed so that a weight of the actual-measurement dose-calibration factor $\alpha_i$ at a deep layer among the actual-measurement dose-calibration factors $\alpha_i$ is larger than a weight of the actual-measurement dose-calibration factor $\alpha_i$ at a shallow layer there among. Thus, even for the layer for which no actual dose has been measured, the dose can be calibrated using a precise factor for calibration of dose, so that it is possible to achieve a highly accurate irradiation in line with the treatment plan.

Embodiment 2

Figure 6:
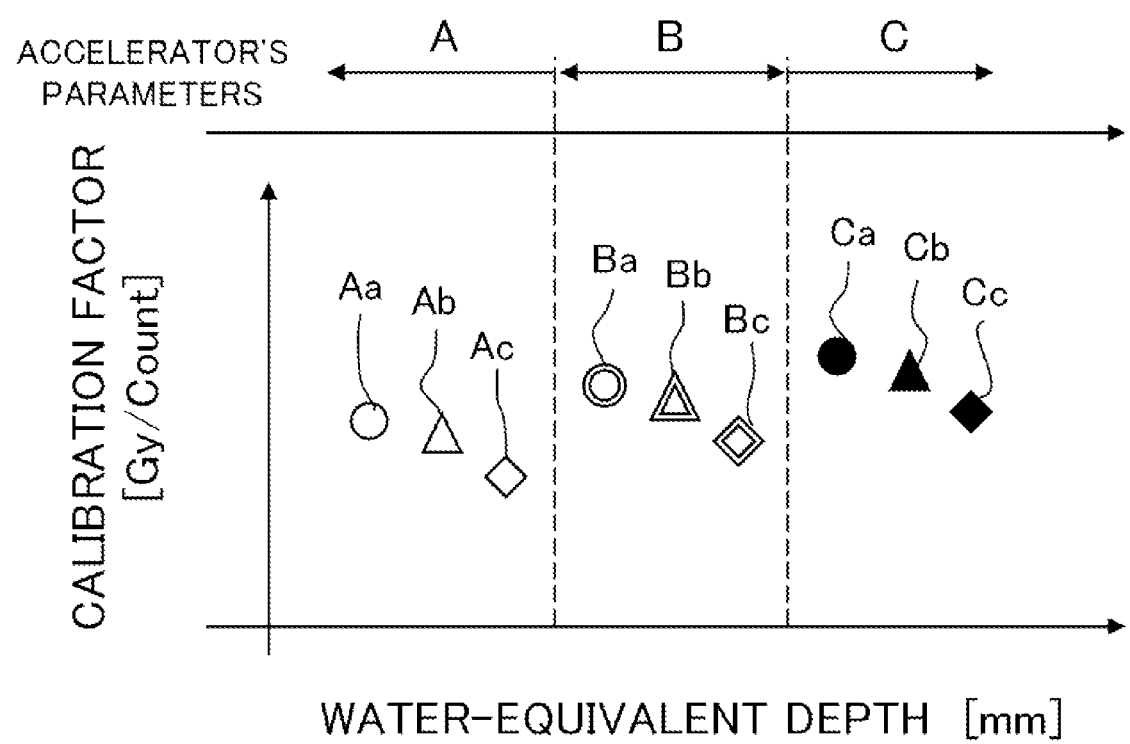
FIG. 6 is a graph representing a relationship between water-equivalent depths of respective layers with different irradiation conditions and actually-measured dose calibration factors, with respect to a particle therapy device according to Embodiment 2 of the invention.

In Embodiment 1, the description has been made about a case where, at the calculation of the interpolation value $\beta_i$, weighting is performed with attention to the water-equivalent depth; however, in Embodiment 2, weighting is performed in consideration also of an irradiation condition other than the water-equivalent depth. FIG. 6 is for illustrating a particle therapy device or a method for setting a dose calibration factor according to Embodiment 2, and is a graph representing schematically a relationship between water-equivalent depths of respective layers with different irradiation conditions with respect to the particle therapy device and actually-measured dose calibration factors. Note that, for the configuration related to the particle therapy device and its control, the figures used in Embodiment 1 will also be used, and similar parts therein will be omitted from description.

In Embodiment 2, focusing is taken to the fact that, when a variation occurs in water-equivalent depth, a range of the particle beam (a position of the Bragg peak) is adjusted for achieving irradiation at that water-equivalent depth, so that a dose distribution varies. Factors for varying the dose distribution depending on the range of the radiated particle beam, include, <1> Fan Beam Effect or Cone Beam Effect, <2> Difference in Type (Thickness) of Range Shifter 15 in Use, and <3> Difference in Wobbler Radius (in the case of a layer-stacking conformal irradiation). In the followings, description will be made about them, respectively.

<1> Fan Beam Effect or Cone Beam Effect

As described previously, the irradiation apparatus 10 serves to form the pencil-like narrow beam supplied from the accelerator 30 into that matched to a shape of the diseased site, so as to achieve the dose distribution planned for treatment. Thus, the supplied beam is enlarged in x-y direction by a scatterer or a wobbler electromagnet (broad beam method (including the case of a layer-stacking conformal irradiation)) placed in the lateral-direction irradiation-field forming unit 11, or scanned in x-y direction by a scanning electromagnet (scanning method) placed therein.

Accordingly, the beam that will reach the irradiation target from the irradiation apparatus 10 is not parallel, and is radiated so that it passes a region spread in a fan-like or cone-like manner by the scatterer/the wobbler electromagnet or the scanning electromagnet. Accordingly, this results in difference of the dose distribution (this may be assumed to be a number of particles per unit area) due to difference in the range, even if the intensity of the original pencil-like narrow beam is unchanged (the number of particles per unit time is unchanged). Thus, even when the measurement value $C_i$ (corresponding to the number of particles) counted by the dose monitor 12 placed in the irradiation apparatus 10 is unchanged, different ranges result in different dose distributions given to the patient. This fact is called a fan beam effect or a cone-beam effect.

<2> Effect Due to Difference in Type (Thickness) of Range Shifter in Use

As methods for changing the range of the particle beam, there are two methods. The first one is a method for changing the kinetic energy of the particles accelerated in the accelerator 30-side. The second one is a method for causing the particle beam supplied with a given energy to pass the range shifter 15 having a different thickness, to thereby adjust an amount of loss in the kinetic energy that the particles have. The method by using the accelerator 30 is suited to roughly adjust the energy level, whereas the method by changing the type of the range shifter 15 is suited to finely adjust the energy level. In the actual apparatus, it is general to use these two methods together.

The range shifter 15 is placed, as the depth-direction irradiation-field forming unit 13, in the irradiation apparatus 10, and starts spreading the particle beam at the time it passes the range shifter 15. The degree of this spreading depends largely on the thickness of the range shifter 15, which also results in different dose distributions due to difference in the thickness of the range shifter 15. The degree of the spreading particularly largely changes at the difference between the case of not using the range shifter 15 at all and the case of using the range shifter 15. In order to avoid this influence as much as possible, even in the case of the target energy for which the range shifter 15 is not necessary, it is also effective to nevertheless add a thin range shifter 15 as a dummy.

<3> Difference in Wobbler Radius (in the case of a Broad Beam Method, such as a Layer-Stacking Conformal Irradiation)

As described previously, in the case of the broad beam method, in order to achieve the dose distribution planned for treatment in conformity with the shape of diseased site, the pencil-like narrow beam supplied to the irradiation apparatus 10 is enlarged in x-y direction using a wobbler electromagnet or the like. In more particular, the wobbler electromagnet causes the pencil-like narrow beam to scan, for example, in a circular motion, and then, the particle beam is radiated so as to pass the scatterer. This achieves mostly uniform dose distribution in the enlarged irradiation field. The radius in the circular motion of the beam is called "wobbler radius".

Thereafter, the irradiation field is formed to be matched to the shape of diseased site of the patient, in such a manner that its unnecessary portion is blocked off by a collimator or the like. On this occasion, it is sufficient that the size of the irradiation field having such a uniform dose distribution be large to such an extent capable of fully enclosing the diseased site of the patient. Thus, in consideration of the utilization efficiency of the beam, it is allowed to intentionally change the wobbler radius depending on the size of the diseased site (or each layer) of the patient. This wobbler radius is also a factor by which the dose distribution varies.

Description will be made about how the above factors <1> to <3> would influence, citing a case of a layer-stacking conformal irradiation. The diseased site of the patient, as an irradiation target, is partitioned into some virtual slices (layers) in a beam-axis direction (depth direction, z-direction). For simplicity's sake, numbers are given to the slices (1, 2, ... n, from the distal side). Although it is not necessary that this order (from the distal side) be always an order of irradiation for the slices, the order of irradiation preformed from the distal side is well adopted in medical scenes. In order to achieve radiation to each slice, the energy of the particle beam is adjusted as the range (position of the Bragg peak) of the radiation beam. While the energy of the particle beam is to be adjusted using the accelerator 30 and the range shifter 15 together as described previously, on this occasion, a parameter of the accelerator 30 and the range shifter 15 to be used are determined.

What dose calibration factor is used for each of the virtual slices at the treatment, is determined through prior measurement (in the calibration stage) using the water phantom 81. Here, for that dose calibration factor, although it is conceivable to calculate the interpolation value $\beta_i$ as described in Embodiment 1 using the polynomial model (formula (2)) that uses a water-equivalent depth as a parameter, a problem of non-consecutiveness arises in a dose-calibration factor characteristic curve, due to the irradiation method, such as the aforementioned energy adjusting method, etc. In the followings, description will be made using FIG. 6.

FIG. 6 is a graph schematically representing a relationship between the dose calibration factor $\alpha_i$ calculated in the calibration stage on the basis of the actually measured result using the water phantom 81 and the water-equivalent depth $x_i$. In the figure, the abscissa represents the water-equivalent depth $x_i$ [mm WEL] (the depth of the calibration dosimeter 82 in the water phantom 81 from the water surface) and the ordinate represents a value resulted from dividing the dose [Gy] obtained by the calibration dosimeter 82 by the measurement value $C_i$ [Count] of the dose monitor 12 placed in the irradiation apparatus 10.

Further, for simplicity's sake, here is assumed that the parameters of the energy of the particle beam emitted from the accelerator 30 (accelerator's parameters) are of three types: A, B and C, and the types of the thickness and material of the range shifter 15 (range-shifter's parameters) are three types: a, b and c. The respective plots indicate the measurement result, and from the left side (shallow in the water-equivalent depth) to the right side (deep in the water-equivalent depth), correspond to the data under conditions of Aa, Ab, Ac, Ba, Bb, Bc, Ca, Cb and Cc. With the characteristic curve of the dose calibration factor obtained in the case of such layer-dependent different conditions, there is a problem that, when it is to be totally approximated by a single polynomial equation, non-consecutiveness has arisen in its characteristic.

Here, if focusing only to the data (Aa, Ab, Ac) corresponding to the parameter A among the accelerator's parameters, non-consecutiveness does not arise in its characteristic, so that it is possible to achieve modeling precisely using a single polynomial equation. Further, if focusing only to the data (Aa, Ba, Ca) corresponding to the parameter a among the range-shifter's parameters, non-consecutiveness does not arise in its characteristic, so that it is also possible to achieve precise modeling similarly using a single polynomial equation. Namely, when data is divided into groups depending on the accelerator's parameter or the range-shifter's parameter, followed by preparing to store a polynomial equation of the dose-calibration factor characteristic curve corresponding to the group using the data of the same group, it is possible to resolve the problem of the non-consecutiveness, to thereby obtain the interpolation value $\beta_i$ with excellent accuracy.

Although the description has been made based on FIG. 6 about the grouping by the accelerator's parameter and the grouping by the range-shifter's parameter, because a similar problem of non-consecutiveness arises due to a difference in wobbler radius (wobbler-radius parameter), a grouping by the wobbler-radius parameter is also usable of course.

Namely, according to an irradiation condition (parameter) of a layer that requires the interpolation value $\beta_i$, the weight setting unit 75 described with FIG. 3 sets to zero the weights of dose calibration factors $\alpha_i$ for layers whose conditions are different to that irradiation condition. This makes it possible to resolve the problem of non-consecutiveness to thereby obtain the interpolation value $\beta_i$ with excellent accuracy, so that a highly accurate irradiation in line with the treatment plan can be achieved.

As described above, in accordance with the particle therapy device according to Embodiment 2, the interpolation value generation unit 74 is configured to perform weighting on each of the actual-measurement dose-calibration factors $\alpha_i$, for each layer subject to the interpolation value $\beta_i$, on the basis of commonality in any one or any combination of the accelerator's parameter for adjusting the energy, the range-shifter's parameter and the wobbler radius parameter for adjusting the size of the irradiation field, as irradiation conditions for said each layer, in addition to the depth as described previously. Thus, even for the layer for which no actual dose has been measured, since the dose can be calibrated precisely, it is possible to achieve a highly accurate irradiation in line with the treatment plan.

Further, in accordance with the method for setting a dose calibration factor according to Embodiment 2, in the interpolation value generation step, it is designed to perform weighting on each of the actual-measurement dose-calibration factors $\alpha_i$, for each layer subject to the interpolation value $\beta_i$, on the basis of commonality in any one or any combination of the accelerator's parameter for adjusting the energy, the range-shifter's parameter and the wobbler radius parameter for adjusting the size of the irradiation field, as irradiation conditions for said each layer, in addition to the depth as described previously. Thus, even for the layer for which no actual dose has been measured, since the dose can be calibrated using a precise factor for calibration of dose, it is possible to achieve a highly accurate irradiation in line with the treatment plan.

Embodiment 3

In Embodiment 2, the description has been made about a case of using only the dose calibration factors of the layers whose conditions are the same as that of a layer that wants to obtain the interpolation value. However, in practice, the region required for the polynomial model is a region having a specified width that is "deeper than the depth allowable for measurement by the water phantom". Thus, in that region, an influence due to a plurality of parameters exists. Namely, in that region, an influence emerges due to "accelerator's parameter", "range-shifter's parameter", "wobbler radius parameter", etc., in their overlapped manner. Thus, in the particle therapy device or the method for calibrating an irradiation dose according to Embodiment 3, a black/white decision is not taken whether "to use/not to use" each dose calibration factor as data for obtaining the interpolation value, but weighting is taken on the factor in view of a plurality of conditions. Note that, also in Embodiment 3, for the configuration related to the particle therapy device and its control, the figures used in Embodiment 1 will also be used, and similar parts therein will be omitted from description.

For simplifying description, description will be made about a case where weighting is performed when the irradiation conditions are narrowed to two conditions of the accelerator's parameter and the wobbler radius parameter.

Here, the layer (slice) that wants to obtain the interpolation value $\alpha_i$ is assumed to be a deeper layer (distal side) than the water-equivalent depth allowable for measurement by the water phantom 81. As to the accelerator's parameter, as described with FIG. 6, there are three conditions of A, B and C from the shallow side of the water-equivalent depth toward the deep side thereof. Further, the accelerator's parameter for deeper layers (distal side) than the water-equivalent depth allowable for measurement is assumed to C. Accordingly, as a unit coefficient to be used at the time of setting the weight, 1.0 is set in the cases of a common condition of C; and with respect to different conditions of B and A, 0.8 is set in the nearer-depth cases of B, and 0.5 is set in the farthest cases of A.

Meanwhile, as to the wobbler radius parameter, there are three conditions of X mm, X+20 mm and X+40 mm from the small side of the radius toward the large side thereof. Further, the radius is assumed to X mm at the time of achieving irradiation of a distal-side layer that wants to obtain the interpolation value $\beta_i$. Accordingly, as a unit coefficient to be used at the time of setting the weight, 1.0 is set in the cases of a common condition of X mm; with respect to other two different conditions, 0.4 is set in the cases of X+20 mm that is nearer to X, and 0.2 is set in the most different cases of X+40 mm.

When the unit coefficient for weighting is set for each type of the respective parameters in this manner, and when each actual-measurement dose-calibration factor $\alpha_i$ is multiplied by the unit coefficient for each parameter according to the combination of irradiation conditions, it becomes possible to perform weighting as shown in Table 1.

TABLE 1

Examples of Combination in Condition and Weighting

| Condition | | Accelerator's Parameter | | |
|---|---|---|---|---|
| | | C | B | A |
| Wobbler Radius | X mm | 1 | 0.8 | 0.5 |
| | X + 20 mm | 0.4 | 0.32 | 0.2 |
| | X + 40 mm | 0.2 | 0.16 | 0.1 |

Note that, in order to perform the aforementioned calibration, for example, the respective unit coefficients, etc., are stored in the dose data processing unit 71, as well as the calibration factor calculation unit 77 is, at the time of calculating the dose calibration factor $\alpha_i$, caused to associate it with the data of the irradiation condition (s). Accordingly, in the weight setting unit 75, when the associated data-based reflection is applied to the definition of W in the formula (D2), the weight of the dose calibration factor $\alpha_i$ can be adjusted according to the irradiation condition (s) of the layer that wants the interpolation value $\beta_i$. This makes it possible to obtain the interpolation value $\beta_i$ with excellent accuracy while taking into consideration the total characteristic in view of the problem of non-consecutiveness and the influence by the plurality of conditions, so that a highly accurate irradiation in line with the treatment plan can be achieved.

As described above, in accordance with the particle therapy device according to Embodiment 3, the interpolation value generation unit 74 is configured: to determine the unit coefficients for weighting, on the basis of commonality about each of the depth, the accelerator's parameter for adjusting the energy, the range-shifter's parameter and the wobbler radius parameter for adjusting the size of the irradiation field, as irradiation conditions; and to perform, for each layer subject to the interpolation value $\beta_i$, weighting on each of the actual-measurement calibration factors $\alpha_i$ according to a combination of the respective parameters, using the value multiplied by each of the unit coefficients. Thus, a dose can be calibrated precisely even for the layer for which no actual dose has been measured, so that it is possible to achieve a highly accurate irradiation in line with the treatment plan.

Further, in accordance with the method for setting a dose calibration factor according to Embodiment 3, in the interpolation value generation step, it is designed: to determine the unit coefficients for weighting, on the basis of commonality about each of the depth, the accelerator's parameter for adjusting the energy, the range-shifter's parameter and the wobbler radius parameter for adjusting the size of the irradiation field, as irradiation conditions; and to perform, for each layer subject to the interpolation value $\beta_i$, weighting on each of the actual-measurement calibration factors $\alpha_i$ according to a combination of the respective parameters, using the value multiplied by each of the unit coefficients. Thus, a dose can be calibrated using a precise factor for calibration of dose even for the layer for which no actual dose has been measured, so that it is possible to achieve a highly accurate irradiation in line with the treatment plan.

As described above, in accordance with the particle therapy devices according to the respective Embodiments 1 to 3, there is provided a particle therapy device 1 in which an irradiation target is partitioned into a plurality of layers in order of depth from a body surface, and irradiation is performed while an irradiation dose is controlled for each of the layers, said particle therapy device configured to include: the irradiation apparatus 10 that radiates a particle beam supplied from the accelerator 30, after forming the beam for said each of the layers; the dose monitor 12 that is placed in the irradiation apparatus 10 and measures a dose in real time; the dose evaluation unit 70 that evaluates the irradiation dose for said each of the layers on the basis of a dose that is calculated using the measurement value $C_i$ measured by the dose monitor 12 and using the dose calibration factor ($\alpha_i$, $\beta_i$) set for said each of the layers, and a dose determined by a treatment plan; an irradiation control device (the irradiation control section 60) that controls a irradiation amount to said each of the layers on the basis of an evaluation result of the dose evaluation unit 70; and the interpolation value generation unit 74 that uses actual-measurement dose-calibration factors $\alpha_i$ each obtained by radiating a particle beam to a simulated phantom (the water phantom 81) provided with the calibration dosimeter 82, to thereby generate the interpolation value $\beta_i$ of the dose calibration factor for at least one of the layers for which the actual-measurement dose-calibration factor $\alpha_i$ is not obtained;

wherein, for each layer subject to the interpolation value $\beta_i$ and based on an irradiation condition of that layer, the interpolation value generation unit 74 performs weighting on each of the actual-measurement dose-calibration factors. Thus, a dose can be calibrated precisely even for the layer for which no actual dose has been measured, so that it is possible to achieve a highly accurate irradiation in line with the treatment plan.

Further, in accordance with the methods for setting a dose calibration factor according to the respective Embodiments 1 to 3, there is provided a method for setting a dose calibration factor ($\alpha_i$, $\beta_i$), that is used in a particle beam therapy in which an irradiation target is partitioned into a plurality of layers in order of depth from a body surface and irradiation is performed while an irradiation dose is controlled for each of the layers, and that is for calculating a dose in the irradiation target using a measurement value $C_i$ of the dose monitor 12 placed in the irradiation apparatus 10;

said method is designed to include: a step of radiating a particle beam to a simulated phantom (water phantom 81) provided with the calibration dosimeter 82 to thereby obtain actual-measurement dose-calibration factors $\alpha_i$ each using a depth $x_i$ of the calibration dosimeter 82 in the simulated phantom (water phantom 81) as a parameter, on the basis of the measurement value $C_i$ of the dose monitor 12 and the measurement value (physical dose $D_i$) of the calibration dosimeter 82; and an interpolation value generation step of establishing a mathematical function (formula (2)) of the dose calibration factor $\alpha_i$ having a depth $x_i$ as a variable, on the basis of the actual-measurement dose-calibration factors $\alpha_i$, to thereby generate the interpolation value $\beta_i$ of the dose calibration factor corresponding to the layer for which the actual-measurement dose-calibration factor $\alpha_i$ is not obtained;

wherein, in the interpolation value generation step, for the layer subject to the interpolation value $\beta_i$ and based on an irradiation condition corresponding to that layer, weighting is performed on each of the actual-measurement dose-calibration factors $\alpha_i$. Thus, even for the layer for which no actual dose has been measured, the dose can be calibrated using a precise factor for calibration of dose, so that it is possible to achieve a highly accurate irradiation in line with the treatment plan.

DESCRIPTION OF REFERENCE NUMERALS and SIGNS

1: particle therapy device, 10: irradiation apparatus, 11: lateral-direction irradiation-field forming unit, 12: dose monitor, 13: depth-direction irradiation-field forming unit, 14: ridge filter, 15: range shifter, 20: particle beam transport section, 30: accelerator, 40: position control section, 41: treatment table, 50: treatment plan section, 60: irradiation control section, 70: dose evaluation unit, 71: dose data processing unit, 72: evaluating unit, 73: dose calculation unit, 74: interpolation value generation unit, 75: weight setting unit, 76: interpolation value calculation unit, 77: calibration factor calculation unit, 80: calibration device, 81: water phantom (simulated phantom), 82: calibration dosimeter, $C_i$: measurement value, $D_i$: physical dose, IC: isocenter, K: patient, $\alpha_i$: actual-measurement dose-calibration factor (factor for calibration of dose), interpolation value (interpolation value or $\alpha_i$: estimation value (factor for calibration of dose)).

The invention claimed is:

1. A particle therapy device in which an irradiation target is partitioned into a plurality of layers in order of depth from a body surface, and irradiation is performed while an irradiation dose is controlled for each of the layers, comprising:
an irradiation apparatus that radiates a particle beam supplied from an accelerator, after forming the beam for said each of the layers;
a dose monitor that is placed in the irradiation apparatus and measures a dose in real time;
a dose evaluation unit that evaluates the irradiation dose for said each of the layers on the basis of a dose that is calculated using a measurement value measured by the dose monitor and using a dose calibration factor set for said each of the layers, and a dose determined by a treatment plan;
an irradiation control device that controls a irradiation amount to said each of the layers on the basis of an evaluation result of the dose evaluation unit; and
an interpolation value generation unit that uses actual-measurement dose-calibration factors each obtained by radiating a particle beam to a simulated phantom provided with a calibration dosimeter, to thereby generate an interpolation value or an estimation value of the dose calibration factor for at least one of the layers for which the actual-measurement dose-calibration factor is not obtained;
wherein, for each layer subject to the interpolation value or the calibration value, based on an irradiation condition of that layer, the interpolation-value generation unit performs weighting on each of the actual-measurement dose-calibration factors.

2. The particle therapy device according to claim 1, wherein, when generating the interpolation value or the calibration value for the layer whose depth is deeper than a predetermined value, the interpolation value generation unit performs said weighting so that a weight of the actual-measurement dose-calibration factor at a deep layer among the actual-measurement dose-calibration factors is larger than a weight of the actual-measurement dose-calibration factor at a shallow layer thereamong.

3. The particle therapy device according to claim 2, wherein:
a range shifter for adjusting energy of the particle beam is provided in the irradiation apparatus, and
the interpolation value generation unit performs said weighting on the basis of at least one condition from among the energy of the particle beam emitted from the accelerator, a thickness of the range shifter and a material thereof.

4. The particle therapy device according to claim 2, wherein:
a wobbler electromagnet for enlarging a diameter of an irradiation field of the particle beam is provided in the irradiation apparatus, and
the interpolation-value generation unit performs said weighting on the basis of the enlarged diameter.

5. The particle therapy device according to claim 3, wherein:
a wobbler electromagnet for enlarging a diameter of an irradiation field of the particle beam is provided in the irradiation apparatus, and
the interpolation-value generation unit performs said weighting on the basis of the enlarged diameter.

6. The particle therapy device according to claim 1, wherein:
a range shifter for adjusting energy of the particle beam is provided in the irradiation apparatus, and
the interpolation value generation unit performs said weighting on the basis of at least one condition from among the energy of the particle beam emitted from the accelerator, a thickness of the range shifter and a material thereof.

7. The particle therapy device according to claim 6, wherein:
a wobbler electromagnet for enlarging a diameter of an irradiation field of the particle beam is provided in the irradiation apparatus, and
the interpolation-value generation unit performs said weighting on the basis of the enlarged diameter.

8. The particle therapy device according to claim 1, wherein:
a wobbler electromagnet for enlarging a diameter of an irradiation field of the particle beam is provided in the irradiation apparatus, and
the interpolation-value generation unit performs said weighting on the basis of the enlarged diameter.

9. A method for setting a dose calibration factor that is used in a particle beam therapy in which an irradiation target is partitioned into a plurality of layers in order of depth from a body surface and irradiation is performed while an irradiation dose is controlled for each of the layers, and that is for calculating a dose in the irradiation target using a measurement value of a dose monitor placed in an irradiation apparatus; said method comprising:
a step of radiating a particle beam to a simulated phantom provided with a calibration dosimeter to thereby obtain actual-measurement dose-calibration factors each using a depth of the calibration dosimeter in the simulated phantom as a parameter, on the basis of the measurement value of the dose monitor and a measurement value of the calibration dosimeter; and
an interpolation value generation step of establishing a mathematical function of the dose calibration factor having the depth as a variable, on the basis of the actual-measurement dose-calibration factors, to thereby generate an interpolation value or an estimation value of the dose calibration factor corresponding to a layer for which the actual-measurement dose-calibration factor is not obtained;
wherein, in the interpolation value generation step, for the layer subject to the interpolation value or the calibration value, based on an irradiation condition corresponding to that layer, weighting is performed on each of the actual-measurement dose-calibration factors.

10. The method for setting a dose calibration factor according to claim 9, wherein, in the interpolation value generation step, at the time of generating the interpolation value or the calibration value for the layer whose depth is deeper than a predetermined value, said weighting is performed so that a weight of the actual-measurement dose-calibration factor at a deep depth of the calibration dosimeter among the actual-measurement dose calibration factors, is larger than a weight of the actual-measurement dose-calibration factor at a shallow depth thereof.

11. The method for setting a dose calibration factor according to claim 10, wherein, in the interpolation value generation step, said weighting is performed on the basis of the irradiation condition corresponding to said that layer, using a value multiplied by a unit coefficient that has been determined for every set of plural conditions constituting the irradiation condition.

12. The method for setting a dose calibration factor according to claim 10, wherein:
in the particle beam therapy, energy of the particle beam is adjusted using a range shifter; and
in the interpolation value generation step, said weighting is performed on the basis of at least one condition from among the energy of the particle beam emitted from an accelerator, a thickness of the range shifter and a material thereof.

13. The method for setting a dose calibration factor according to claim 10, wherein:
in the particle beam therapy, a diameter of an irradiation field of the particle beam is enlarged by a wobbler electromagnet; and
in the interpolation value generation step, said weighting is performed on the basis of the enlarged diameter.

14. The method for setting a dose calibration factor according to claim 12, wherein:
in the particle beam therapy, a diameter of an irradiation field of the particle beam is enlarged by a wobbler electromagnet; and
in the interpolation value generation step, said weighting is performed on the basis of the enlarged diameter.

15. The method for setting a dose calibration factor according to claim 12, wherein, in the interpolation value generation step, said weighting is performed on the basis of the irradiation condition corresponding to said that layer, using a value multiplied by a unit coefficient that has been determined for every set of plural conditions constituting the irradiation condition.

16. The method for setting a dose calibration factor according to claim 9, wherein:
in the particle beam therapy, energy of the particle beam is adjusted using a range shifter; and
in the interpolation value generation step, said weighting is performed on the basis of at least one condition from among the energy of the particle beam emitted from an accelerator, a thickness of the range shifter and a material thereof.

17. The method for setting a dose calibration factor according to claim 16, wherein:
in the particle beam therapy, a diameter of an irradiation field of the particle beam is enlarged by a wobbler electromagnet; and
in the interpolation value generation step, said weighting is performed on the basis of the enlarged diameter.

18. The method for setting a dose calibration factor according to claim 16, wherein, in the interpolation value generation step, said weighting is performed on the basis of the irradiation condition corresponding to said that layer, using a value multiplied by a unit coefficient that has been determined for every set of plural conditions constituting the irradiation condition.

19. The method for setting a dose calibration factor according to claim 9, wherein:
in the particle beam therapy, a diameter of an irradiation field of the particle beam is enlarged by a wobbler electromagnet; and
in the interpolation value generation step, said weighting is performed on the basis of the enlarged diameter.

20. The method for setting a dose calibration factor according to claim 9, wherein, in the interpolation value generation step, said weighting is performed on the basis of the irradiation condition corresponding to said that layer, using a value multiplied by a unit coefficient that has been determined for every set of plural conditions constituting the irradiation condition.

* * * * *